United States Patent [19]

Hamel et al.

[11] Patent Number: 5,059,031

[45] Date of Patent: Oct. 22, 1991

[54] HIGH-SPEED OPTICAL TESTING OF OBJECTS

[75] Inventors: Jean-Pierre Hamel, Maisons-Laffitte; Pierre Lamborot, Paris, both of France

[73] Assignee: Saint-Gobain Cinematique et Controle, Gennevilliers, France

[21] Appl. No.: 468,532

[22] Filed: Jan. 23, 1990

[30] Foreign Application Priority Data

Jan. 26, 1989 [FR] France .................................. 89 00936

[51] Int. Cl.[5] ........................ G01N 21/90; B07C 5/342
[52] U.S. Cl. ..................................... 356/428; 356/240; 250/223 B; 209/522; 209/526
[58] Field of Search ................ 356/428, 240, 239, 237; 250/223 B, 224; 209/3.1, 522, 525, 526, 528

[56] References Cited

U.S. PATENT DOCUMENTS

3,887,284 6/1975 Gender et al. ....................... 356/240
4,547,067 10/1985 Watanabe ............................. 356/240
4,620,090 10/1986 Ducloux ........................... 250/223 B

*Primary Examiner*—Vincent P. McGraw
*Assistant Examiner*—LaCharles P. Keesce
*Attorney, Agent, or Firm*—Pennie & Edmonds

[57] ABSTRACT

A method and apparatus are described for the optical inspection of at least partially transparent objects, such as bottles or flasks, arranged in line on a moving horizontal table conveyor. A light source is located on one side of the conveyor and a linear electronic camera on the other. The camera comprises a line of photodetectors extending in a first direction. A lens forms on the camera an image of a portion of the object being inspected, the image being oriented so that as the object moves, the image moves in the same direction as the first direction. The image is scanned rapidly and repeatedly in the first direction by electronically scanning the line of photodetectors. The image is scanned in a second direction, preferably perpendicular to the first direction by a pivoting mirror which varies the portion of the object that is imaged onto the photodetectors. Advantageously, the rate of scan in the second direction is varied so that different portions of the object receive different amounts of attention, such variation being effected either by a predetermined program or by some feedback mechanism.

43 Claims, 5 Drawing Sheets

HIGH-SPEED OPTICAL TESTING OF OBJECTS

BACKGROUND OF THE INVENTION

This invention relates to the automatic optical testing of transparent bodies, in particular articles such as bottles or flasks of glass or plastics materials, at high operating rates of the order of 15,000 articles per hour and more.

Many different types of optical testing are known in the industry. Certain very precise checks can only be carried out at relatively low operating rates because it is necessary to use light emitters having a narrow beam and to grip the articles one by one to turn them in front of the apparatus. In many situations, however, such a careful inspection is not necessary and much higher operating rates can be achieved. In such circumstances, it is preferable to observe the articles while moving, without contact, and to limit the checks to those for the most harmful defects, which are those most easily seen. Such defects include deformations, major defects such as fractures or heavy glazing resulting from thermal shocks or handling that are liable to cause breakages in the production line, opacity attributable to the presence of relatively large stones or bubbles, "chicken-costs" that are dangerous to the user, etc.

Such visual tests are presently carried out by direct observation in transparency on a clear background. The defects observed produce more or less luminous stains which are inscribed inside a more uniform image, the darkened outline of which indicates the profile of the object, or which even alter this profile in the case of a broken or deformed article.

The articles to be examined are carried aligned in a row, spaced apart by a suitable spacer means and transported by a horizontal table conveyor through an examination apparatus. The examination apparatus comprises a light source which illustratively is a simple screen providing a luminous background on one side of the row of articles and on the other side of the row a fixed optical receiver system comprising an electronic camera having a short response time. A lens forms a real image of the article on a photosensitive surface of the camera which is raster scanned by electronic means to convert this image into a succession of quantified electrical signals. Analysis of these signals permits detection of anomalies in the articles and dimensional measurements of the outline of the article. In this way it is possible to characterize the nature and magnitude of the defects and, where appropriate, to discard the article.

Since the edges of the image appear darker and perturbed, defects can be detected only in a clear central zone of about 40° to 50° on either side of the optical axis of the examination apparatus and not in the marginal zones. As a result, it is generally necessary to carry out multiple examinations of the articles along two axes intersecting at 90° or even along three axes intersecting at 60°. If the inspections are three in number, at least one rotation of the article is necessary between two of the inspections because it is not possible to align the examination apparatus in a direction too close to the axis of the conveyor.

In view of the variation in shape of the articles to be tested, each camera requires a minimum on the order of 40,000 pixels, of equal or at least very similar sensitivities, to obtain an overall image of satisfactory resolution. Such a camera is expensive both in capital cost and in maintenance since failures lead to a relatively high frequency of replacement of the photosensitive matrices.

Accordingly, it is preferred to use a linear camera in which the photosensitive area is a simple strip or chain of photosensitive diodes, arranged in the form of a single vertical column comprising, for example, $2^8=256$ diodes or $2^9=512$ diodes. In this case, the complete inspection of the article is caused by passing it on the horizontal conveyor in uniform straight translation in front of the apparatus so that successive vertical slices of this article form their image on the vertical column of diodes one after another. The diodes are read by a rapid vertical electronic scan; and the spacing of the analysis columns produced by the successive readings is a function of the speed of passage of the articles and the rate of the scan.

One notable disadvantage of this arrangement is that the dimensional measurements cannot be read until the end of one complete scan of the image. While this scan time is quite short, an article moves enough during the scan for the accuracy of the measurement to suffer from perturbations of mechanical origin such as vibrations, variations in speed of the conveyor, slippage, and of optical or even electrical origin such as shadows, variations in luminous intensity and so on.

SUMMARY OF THE INVENTION

In contrast, the present invention rapidly scans the image of the article in the direction of movement of the article on the conveyor and scans the image more slowly in a direction perpendicular to the direction of movement.

To this end, the camera of an illustrative embodiment of the present invention comprises a row of photosensitive diodes that is aligned virtually parallel to the horizontal direction of movement of the conveyor or transporter, and an optical reflecting system which provides a "vertical" sweeping or scanning movement of the article. Typically, this scanning takes place during a major part of the period during which the bottle passes through the examination apparatus. As a result of this arrangement, a succession of almost instantaneous horizontal scans is obtained, which almost entirely eliminates the disadvantages of the perturbations indicated above.

While movement of the articles, especially at a high uniform speed on a straight conveyor, has the advantage of eliminating erratic movement of the articles, it is still necessary to accommodate this horizontal movement in the camera. In a preferred embodiment of the invention, the camera has a horizontal field considerably greater than the width of the article and the image of the article on the row of photosensitive diodes (i.e., the sequence of horizontal scans) shifts or slides from one side of the row to the other as the article moves past on the conveyor. As a result of the high operating speed of the electronic circuits now commercially available, this sliding can be accommodated, even at very high inspection rates.

Preferably, according to another advantage of the invention, the vertical sweep or scan is governed according to a program determined in advance by the operator or in accordance with a program that can be varied depending on what is observed in the passage of the articles. Such a solution offers the advantage of great flexibility. It is possible to adapt the operating cycle to the article and to inspect the different zones of the article at different speeds and therefore different vertical resolutions that vary according to need.

If desired, the invention may also be practiced using a camera having a two-dimensional array of photosensitive devices.

BRIEF DESCRIPTION OF THE DRAWINGS

These and other objects, features and advantages of the present invention will become more readily apparent from the following detailed description of an advantageous version thereof wherein.

DETAILED DESCRIPTION OF THE INVENTION

The inspection machine of the present invention comprises a conveyor and one or more testing stations. Each testing station comprises a light source and a receiver situated on opposite sides of the track of the conveyor. Each station inspects by transparency a series of articles, spaced apart on the conveyor, without rotating the articles during their inspection.

Advantageously, the receiver is a linear network of photodetectors such as photosensitive diodes. Signals from the photodetectors illustratively control in a known manner an ejector for removing the articles from the conveyor line. Alternatively, they may control a marker indicating those articles that are recognized as defective. In addition, the signals may be converted by each receiver into data, which can be used for establishing manufacturing and defect information and statistics which can be transmitted to the manufacturing stations.

To enable several complementary inspections to be provided, one machine generally comprises several stations. The whole assembly advantageously is managed by a microcomputer.

Figure 1:
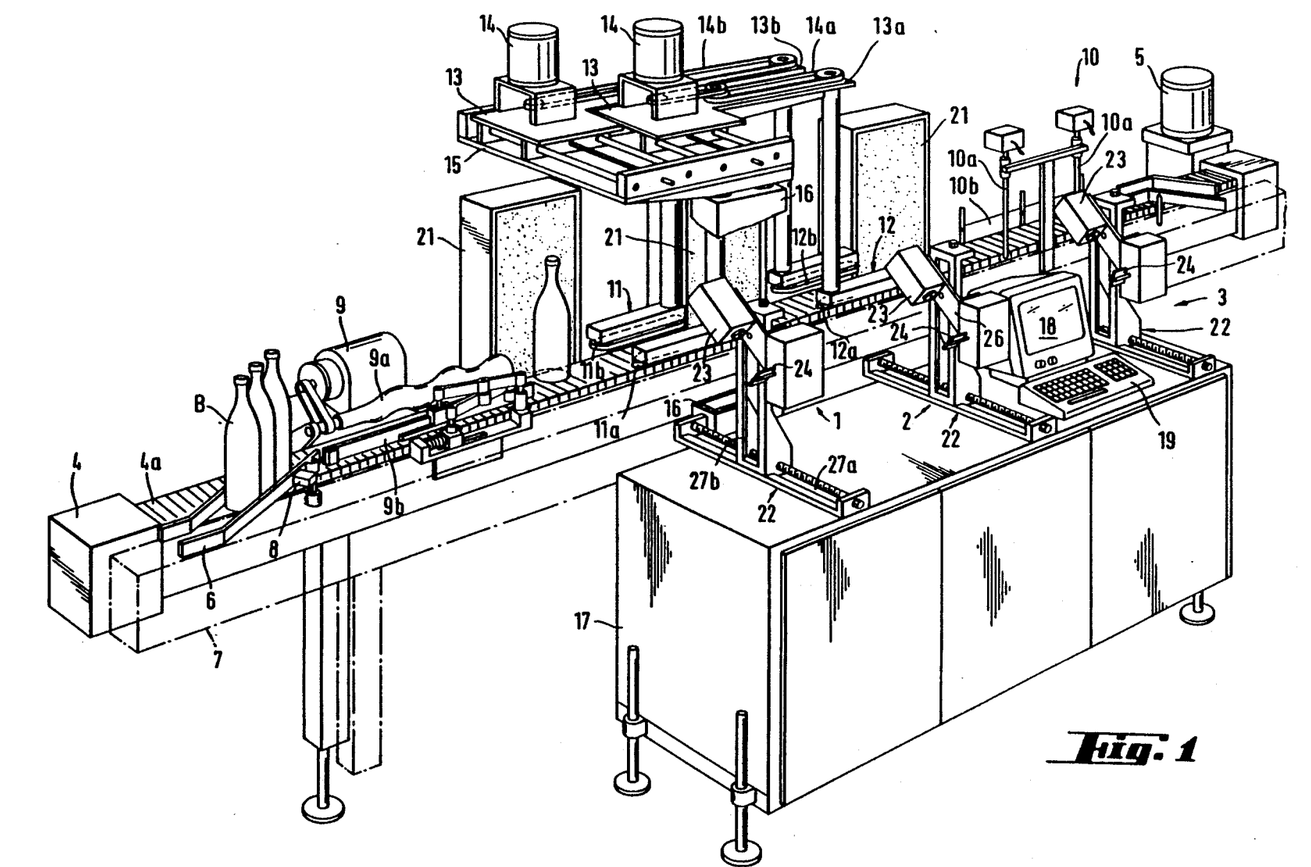
FIG. 1 is a perspective view of a testing machine for bottles according to the present invention.

The machine of FIG. 1 comprises three side-by-side testing stations 1, 2, 3, of identical construction, arranged along a rectilinear conveyor 4 and oriented perpendicularly to the direction of the conveyor. Conveyor 4 comprises sliding pallets, of sufficient accuracy, on which articles to be tested, such as bottles B, are positioned upright. This conveyor is adapted to move the articles in a continuous movement, at constant spacing, so that they may be tested individually at each testing station. The base of the conveyor provides a horizontal reference seating which is as perfect as possible. More complex solutions can be envisaged, but one of the advantages of the machine according to this invention lies in the very simplicity and flexibility of use of such a conveyor.

A motor 5 enables the conveyor to be driven at a uniform, but adjustable speed. Upstream, a switch 6 takes the articles to be tested from a main conveyor 7 and a blocking jack 8 controls their entry into the machine. A spacer 9 distributes the articles uniformly aligned on the conveyor between its screw 9a and its counterguide 9b. Downstream, an ejector 10, shown in the form of a set of two blowers 10a associated with two chutes 10b, eliminates defective articles by sorting them out.

Stations 1, 2 and 3, are separated by two belt rotators 11 and 12, of conventional type, each of which rotates the articles one-third of a revolution without changing the alignment. Trains of opposed belts 11a and 12a, on the one hand, and 11b and 12b, on the other hand, are suspended from one of two carriages 13 by brackets 13a, 11b, respectively, and are coupled to one of two motors 14 by serrated belts 14a, 14b. The carriages 13 slide on a slide platform 15, itself adjustable in height on a column 16. A cabinet 17 supports stations 1, 2 and 3 and contains a microcomputer including a microprocessor, a memory, a screen console 18 and a keyboard 19 which controls all these devices.

Figure 2:
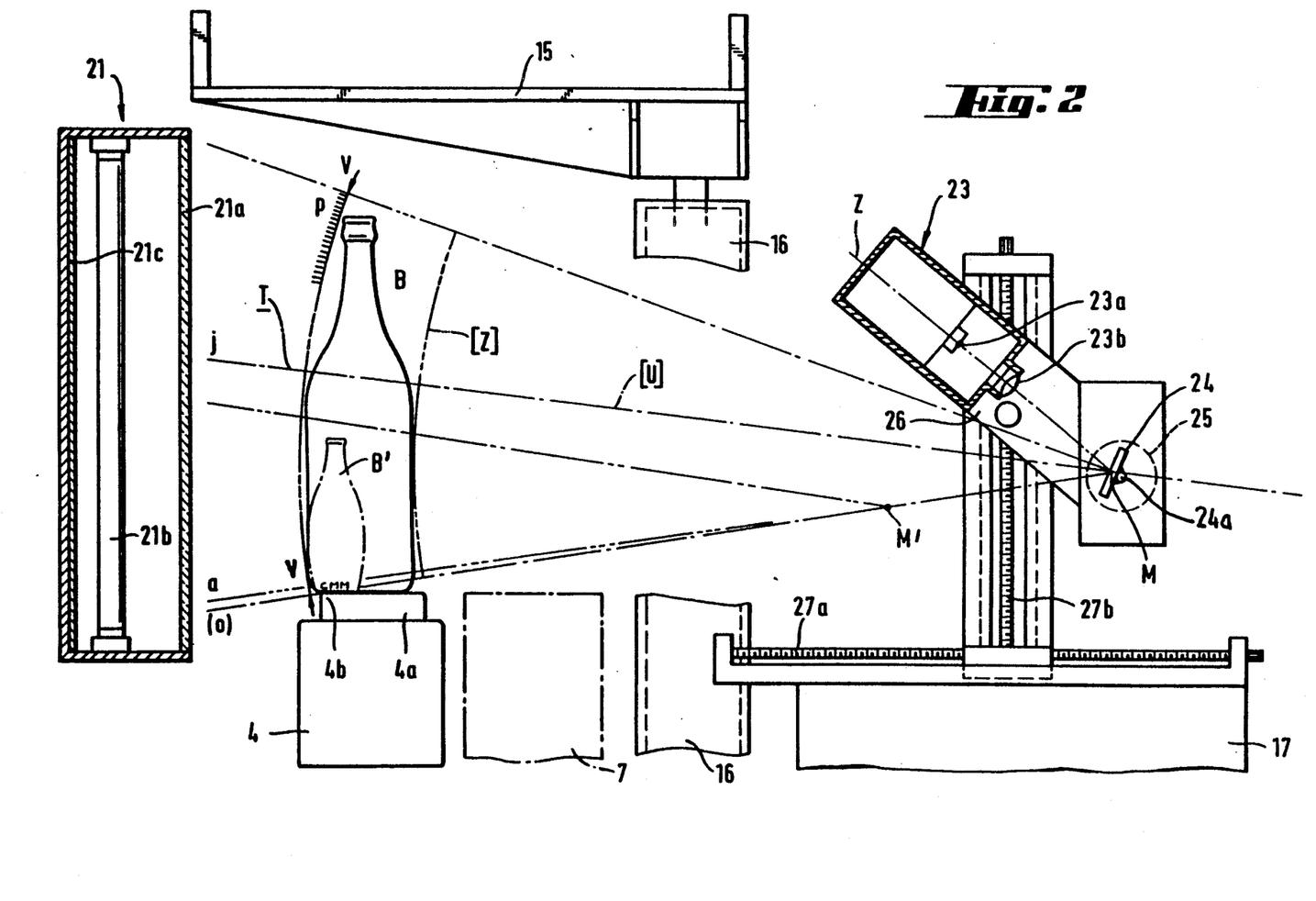
FIG. 2 is a layout of an inspection station of the present invention, in transverse elevation.
Figure 3:
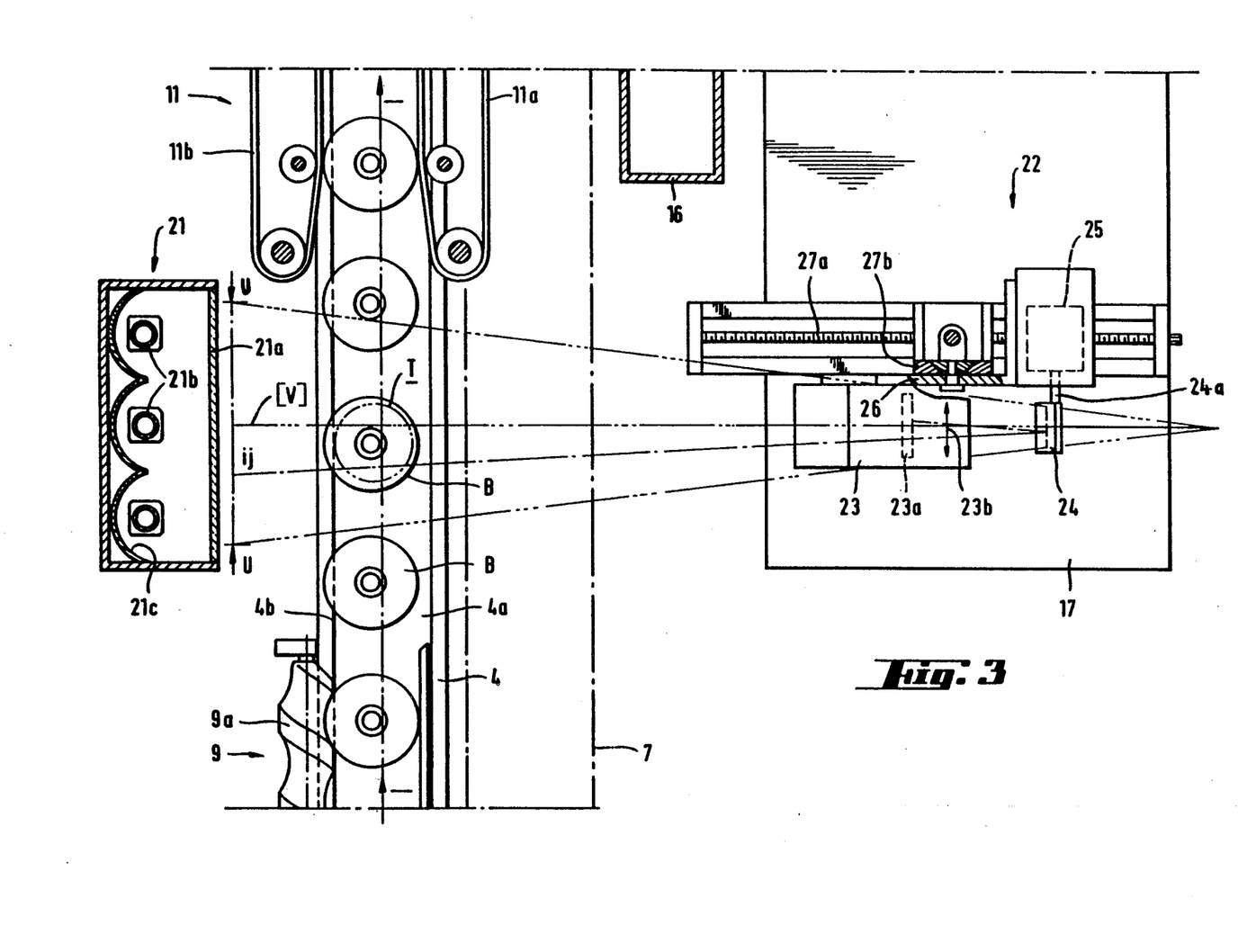
FIG. 3 is a plan layout of this same station.

FIGS. 2 and 3 show in greater detail the arrangement of one of the testing stations, specifically station 1. On one side of conveyor 4 is a light source or emitter 21, comprising essentially a plane, rectangular screen 21a disposed vertically. This screen is of sufficiently large dimensions to cover the whole useful field of vision of the receiver; in practice, as will be seen later, it has a height greater than that of the highest of the articles to be tested and a width on the order of three times the width of the widest article.

The screen is translucent and is illuminated on its rear face by a light box of conventional type, indicated schematically in the form of a series of vertical tubes 21b associated with an optical system 21c. This arrangement is the most suitable for providing a uniform luminosity in space and time.

On the other side of conveyor 4 and opposite to the luminous background produced by the screen 21a, is situated a receiver 22, comprising a linear network camera 23 and a pivoting reflecting mirror 24 mounted on a shaft 24a. Mirror 24 reflects light from screen 21a to camera 23. The camera comprises a lens 23b and a strip of photodetectors such as photosensitive diodes 23a, which constitutes a linear network of receiver photocells. As shown in FIG. 3 the strip of photodetectors and mirror shaft 24a are horizontal and extend in the same direction parallel to the direction of movement of conveyor 4. Accordingly, lens 23b forms on strip 23a an image of a horizontal slice of the light that is reflected by pivoting mirror 24. When there is a bottle on the conveyor, this slice includes a cross section T of the light as modified by passing through the bottle. This image is converted to electric signals by the photodetectors and is read electronically.

The assembly of the optical system of the station 2 has a vertical viewing fan V—V (parallel to the plane of the sheet of FIG. 2) and a plane of symmetry [V] (perpendicular to the plane of the sheet of FIG. 3) perpendicular to the direction of the conveyor. The optical axis Z of lens 23b of the camera is contained in the plane of symmetry. For a fixed position of the mirror and a fixed orientation of camera 23, the mirror 24, lens 23b and strip 23a define a plane of observation [U] (perpendicular to the plane of the sheet of FIG. 2), U—U (FIG. 3) which extends parallel to the direction of the conveyor. This plane of observation intersects the section T on each article B on the conveyor.

Rotation of mirror 24 moves vertically the section of the article that is imaged onto the strip of photodetectors. As a result, the article can be inspected by imaging successive sections onto the strip of photodetectors. In contrast to the prior art where the article is scanned by displacement of the article in the direction of the conveyor (the direction x in FIG. 6), in the present invention the article is scanned by displacement of the image in a direction perpendicular to the conveyor (the vertical direction y in FIG. 6).

A other types of devices may be envisaged for scanning the luminous beam, a rotating plane mirror is the simplest and the one that is most convenient to adjust.

Mirror 24 is rigid but also as light as possible so as to have only small inertia. Its deflection can be up to twenty or even thirty degrees approximately. Its shaft 24a is moved by a programmable mechanism. This may advantageously be a motor 25 subject to a positional control, in particular, a moving coil galvanometer supplied electrically with an adjustable voltage from a voltage divider. Advantageously, a numerical control and a negative feedback loop are used to obtain critical damping with response times of the order of 2 to 3 milliseconds.

Preferably, the vertical sweep or scan of mirror 24 is governed according to a program determined in advance by the operator or in accordance with a program that can be varied depending on what is observed in the passage of the articles. Such a solution offers the advantage of great flexibility. In particular, it is possible to adapt the operating cycle to the article and to inspect the different zones of the article at different speeds and therefore different vertical resolutions that vary according to need just as a human observer would do if performing a manual inspection.

Receiver 22 is mounted on a carriage having crossed slides 27a and 27b which are at right angles to each other and to conveyor 4 and is therefore movable along the plane of symmetry [V] perpendicular to the conveyor 4. Camera 23 can be swiveled about a horizontal axis parallel to conveyor 4 in its mounting on slide 27b; and lens 23b can be adjusted in position or replaced with a different lens to accommodate changes in distance between the lens and the articles on the conveyor. This system of mounting enables the line of aim of the apparatus to be adjusted according to need, and in particular according to the dimensions of the articles, moving for example from M for the large bottles B to M' for the small bottles B'.

Since the stigmatism zone [Z] (FIG. 2) produced by rotation of the mirror 24 is cylindrical, the sight diaphragm of the receiver, which in the present case is the mirror itself, is most commonly placed approximately at mid-height of the article to be inspected. This is the most favorable position for clarity of the image, in view of the limited depth of field which high-sensitivity investigation may demand. In the case of a bottle, a different adjustment may, in certain cases allow an observation of the collar or heel with low obliquity.

Since the two walls of an article on the conveyor are viewed simultaneously by transparency in diffuse light, focusing advantageously is carried out slightly in front of the rear face, so as to balance the sharpness of the image.

FIG. 2 also shows that any bottle B or B' must come into a fixed position near the rear edge 4b of the conveyor, in order to be positioned in the vertical viewing fan V—V. The necessary guidance is provided by the spacer. Nevertheless, the legend zone situated on the perimeter of the heel of the bottle and, if applicable, the indented base of the bottle prevent observations below a height which constitutes the lower limit of inspection. The operator can adjust the vertical fan, with the desired safety margin, by the choice of the extreme addresses of the position control for motor 25 and hence mirror 24.

On each receiver, the row of photodetectors is read and analyzed approximately every 150 to 250 microseconds ($\mu$sec) to form an image line corresponding to the section observed on the article. Since the article moves only a fraction of a millimeter in this time, this time is sufficiently short for each scan to be considered as instantaneous to a first approximation, i.e., the image is not blurred by movement. An inspection phase of 400 to 1,000 scans of lines (distinct or merged) may thus be carried out in approximately 0.1 to 0.2 seconds, which, to the extent to which the information processing is possible in real time, enables practical testing rates of 20,000 to 30,000 articles per hour to be reached.

Since horizontal movement of the articles during examination is not eliminated, the downstream or front edge of each article appears on one side of the receiver field, to disappear subsequently at the opposite side. To accommodate the motion in the camera, the camera has a horizontal field considerable greater than the width of the article. During the inspection, the image observed along the section T slides horizontally across the row of photodetectors from one side to another.

Figure 4:
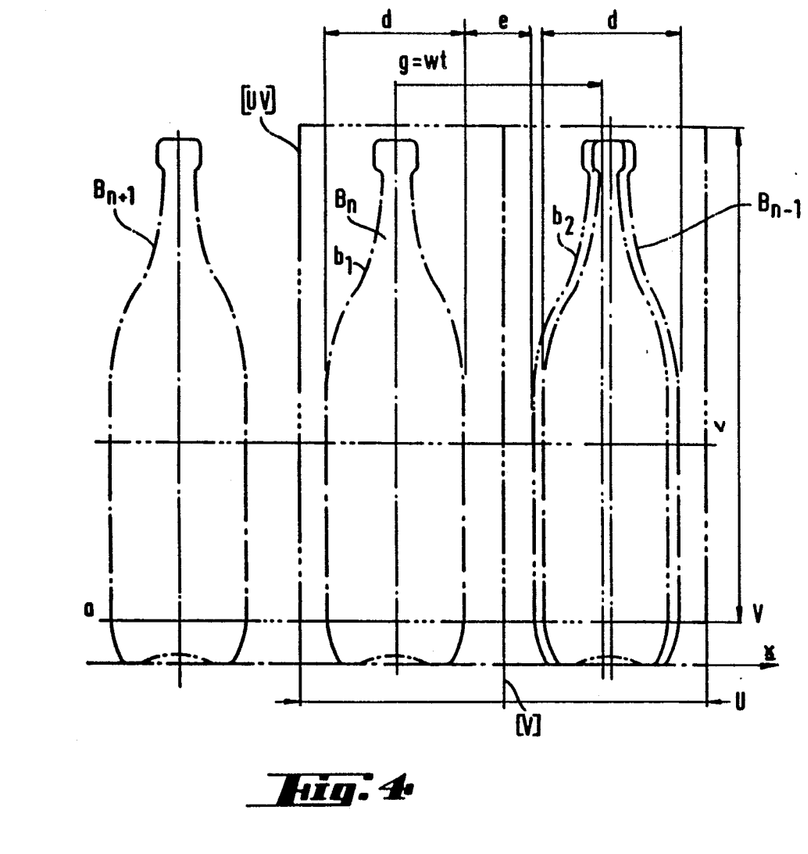
FIG. 4 is an illustration of the passage of successive bottles through the field of the receiver.

To avoid excessively complicated signal processing, it is advantageous to extend the horizontal field of view of the photosensitive cells from the width of the article to be examined to a width equal to at least the width of the article plus its movement. The resulting field of view [UV] is depicted in FIG. 4 where V is the vertical field of view, U is the horizontal field of view, b1 is the initial position of a bottle of diameter d in the field of view and b2 is its final position. During inspection, the bottle moves a distance g which is proportional to the duration t of the inspection cycle and the velocity w of the conveyor. In practice, g is greater than the diameter of the bottle so that there is a gap e between the initial position b1 of the bottle and its final position b2 and the minimum width of the field is given by $U = d + g = 2d + e$.

To achieve maximum throughput of articles through the inspection station, it is desirable to space the articles on the conveyor so that the gap between successive bottles is also close to e. As a result, several articles are simultaneously in the horizontal field of view of the photocells. Since only one of these articles is inspected at a time, an inspection window is used to define which photocells are used in generating an output at any portion of the inspection cycle. This, in turn, requires that the articles on the conveyor be spaced apart relatively precisely. In particular, it is desirable to use a spacer such as a wheel or preferably a distributor screw 9 (FIGS. 1 and 3) to space the articles. Even then, to avoid any risk of interference between successive inspections, the interval e between successive articles cannot be reduced much below one-half of the apparent width d of the articles. As a result, the horizontal field U of the receiver covers a width close to 2.5 d.

Figure 5:
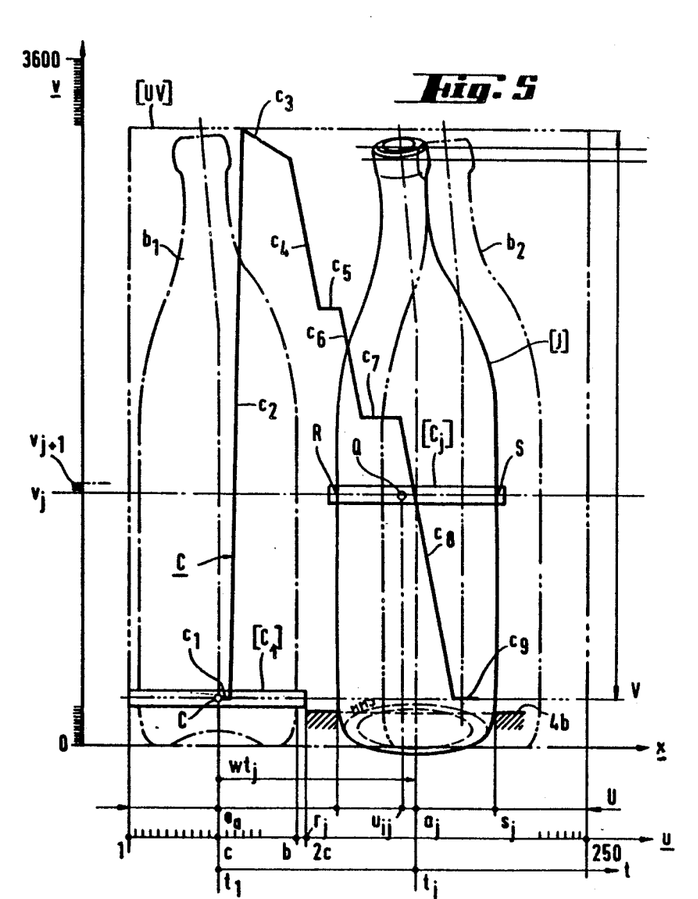
FIG. 5 is an illustration depicting how the testing cycle relates to the feed of a bottle.

FIG. 5 illustrates the scanning procedure. It depicts on field of view [UV] in phantom the initial and final positions b1 and b2 of a bottle as well as in solid line an intermediate position [j] of a bottle. The relation between the field of view and the photodetectors is depicted by 250 photodetectors distributed along the abscissa u below the field of view and the relation between the field of view and the individual scanning lines is depicted by the 3600 lines $v_j$ along the ordinate u to the left of the field of view. Since the position of the bottle in the field of view is also a function of time, a horizontal time axis t is also depicted in FIG. 5. Illustratively, the width of the field of view as measured in the vicinity of the conveyor is about 25 centimeters wide; and in the case where 250 photodetectors are used in strip 23a, the horizontal resolution is therefore one millimeter. Vertical resolution is a function of the accuracy of motor 25 and its control system and typically is four or more times better than the horizontal resolution.

The horizontal section of the bottle that is imaged onto the photodetectors is depicted by a horizontal box $[C_j]$ The projection of this box onto the abscissa indicates the portion of the strip of photodetectors that is used to read the image of this line. In the initial position b1, the section is across the bottom of the bottle.

In conventional manner, pulses emitted by a synchronization timer cause the electric signal voltages from the 250 photodetectors to be read, detector by detector, at predetermined intervals of time. The video signal produced by each reading of the strip is then converted, line by line, into a numerical signal, which is stored in the memory of the microcomputer at a location associated with the address of the scan line concerned.

In the absence of any object in front of the screen, the signal from the photodetectors is flat and since it is higher than a predetermined threshold, it is considered as zero. If, however, an article on the conveyor enters the field of vision of the camera, variations in luminous intensity are caused on the photodetectors, generating a series of detectable signals. During successive scans of the row of photodetectors, different sections of the article are imaged on the row of photodetectors, causing different signals to be generated and stored at storage locations associated with the address of the scan line.

To initiate the testing cycle, a detector monitors the passage of the front or downstream edge of the successive articles. The detector is settled at a height close to the table of the conveyor so that it will detect the passage of all articles reliably, even though they may be broken or overturned, thus preventing any incident. If such a low position is adopted for the starting and reference position of the movement of the mirror, it will be possible to use as the detector a photodetector chosen from the strip of photodetectors.

Illustratively, as shown in FIG. 5, one detector b of the row of photodetectors is chosen to detect the complete arrival of the article, with a slight margin of safety, in the overall field. As soon as this detector is reached by the downstream (front) edge of the image, a signal is emitted that triggers the inspection program.

At this initial instant (instant $t_1$) an inspection window $[C_j]$ of width 2c is created between the cell 1 and cell 2c of the row of photodetectors, framing a segment corresponding to the maximum width d of the bottle and neutralizing all the external cells. In addition, motor 25 which produces the vertical scan of the field by the mirror commences operation in accordance with a user specified control cycle. And inspection window $[C_j]$ commences movement across the row of photodetectors. Since the velocity w of the conveyor is constant and known, the movement of the inspection window across the photodetectors, is at the same relative velocity.

Curve C of FIG. 5 indicates, inside the overall field of view of the receiver, the displacement of the inspection window $[C_j]$ and its aim onto the bottle. It therefore illustrates both the variation in the horizontal direction of the location of the inspection window and the variation in the vertical direction of the section of bottle that is imaged onto the row of photodetectors.

For simplicity of explanation, the curve shown is schematic. In practice it will be necessary in establishing the scanning program to take account of the shift caused by the inertia of the mirror between the real curve and the theoretical track defined in FIG. 5.

As is apparent in FIG. 5, the curve C possesses a sharply ascending portion, and then several descending portions of lesser slope, connecting together a certain number of plateau. The ascending portion is too steep to be used for an inspection. The scan, properly speaking, is carried out only on the return. The descending slopes are dedicated essentially to investigating the defects and the plateau are for dimensional measurements. In effect, they enable the instantaneous readings to be linked to the precise angular lines of sight $v=v_j$ by eliminating the obliquity and in particular, the shift of the investigation or at least by making them negligible. However, it is also possible to calculate the mean of several of these measurements in order to increase accuracy since the movement of the image corresponds to only a fraction of the spacing between successive photodetectors, and even to obtain a vernier effect if the overall horizontal movement during the course of the entirety of these measurements is made to correspond to a predetermined number of photodetector spacings in the horizontal direction. In practice, it is frequently possible to manage with a false plateau.

As shown in FIG. 5, curve C initially has a fairly short plateau $c_1$. It serves to confirm, at the start of the operation, the effective presence of an article of the desired dimension, to determine the position aa of the axis at the height of the heel and to initiate the remainder of the program.

Although the steepness of the slope $c_2$ makes this slope blind, it does enable the top part of the field to be immediately observed. The program first verifies there, by the disappearance of the signal, that the aim is directed to above the bottle. In order to pass through the top of the bottle at minimum speed, the program then starts a slow descent $c_3$, characterized by the fact that the spacing between successive scanning lines is equal to the pitch p of the galvanometer, which gives a vertical spacing smaller than the horizontal movement of each line. The calculation of successive diameters of the bottle then enables the top of the bottle to be located, and therefore its height h to be known. For example, the top may be located by testing for the first diameter greater than a given threshold value, for example three-quarters of the nominal value rather than the first value greater than zero, or by testing for a first difference between diameters on several successive lines.

It is also possible to measure $d_k$, the diameter of the collar, and indeed to record the profile of the collar and to calculate $a_k$, the corresponding position of the axis. Any difference $A_k-A$ then characterizes an overall defect in verticality, the shortness of the time separating the two measurements A and $A_k$ minimizes any errors of mechanical origin.

Less slowly, the remainder of the descent of the mirror is cut into three sections $c_4$, $c_6$ and $c_8$ by two plateau $c_5$ and $c_7$. The first plateau corresponds to a new measurement $A_1$ of the position of the axis, the difference $A_1-A_k$ characterizing a sloping neck; the second plateau provides the measurement $d_m$ of the maximum diameter, and therefore its comparison with the nominal diameter d. Finally, a last plateau $c_9$, observed in the bottom position, corresponds to the return of the mirror to its reference position. It permits the photodetectors at the downstream end of the strip to perform a last measurement $A_z$ on the position of the axis. The total of the differences $A_z-A_a$ represents the difference between the real velocity of the conveyor and its nominal velocity w. It can therefore be used for correcting this set-point value.

Along the three sections $c_4$, $c_6$ and $c_8$, the descent program for the mirror here provides a constant spacing between successive scanning lines that is equal to 4 p, which is still somewhat smaller than that of the horizontal resolution, which is on the order of a millimeter.

After the mirror returns to its initial starting position, the equipment is ready to perform a new testing cycle, even though the first bottle is still in the righthand part of the field. This cycle commences as soon as the detector b gives authorization for it, that is to say as soon as the next bottle appears in the initial position. In practice this occurs after a variable dead time, which can be used by the computer to complete the processing of the whole image provided by the first bottle.

In the duration of one line inspection, the horizontal movement of the image does not reach one quarter of the spacing between successive photodetectors. As a result, by comparing numerical values stored in the computer memory indicative of the ideal effect of the bottle on the luminous intensity detected at the strip of photodetectors, with the signals received from the photodetectors inside the window [$C_j$], it is possible to determine several characteristics of the bottle. In particular, discrepancies indicating anomalies q suggestive of defects Q and their location at abscissae $u_{ij}$ may be calculated. In addition those phenomena $r_j$, $s_j$, indicative of the edge transitions R, S, may be identified by considering these data obtained at a single instant $t_j$. This makes it possible to calculate, from the data read out from the buffer memory, the diameter: $d_j=s_j-r_j$ and position of the axis of the bottle: $2 a_j=s_j+r_j$.

During the course of operation, it is desirable to ignore also the vertical movement and the obliquity produced in each slice observed by the rotation of the mirror. In practice, the spacing between slices should be of the same order as the horizontal resolution, or of the thickness of the slice observed, and preferably be less than this.

Figure 6:
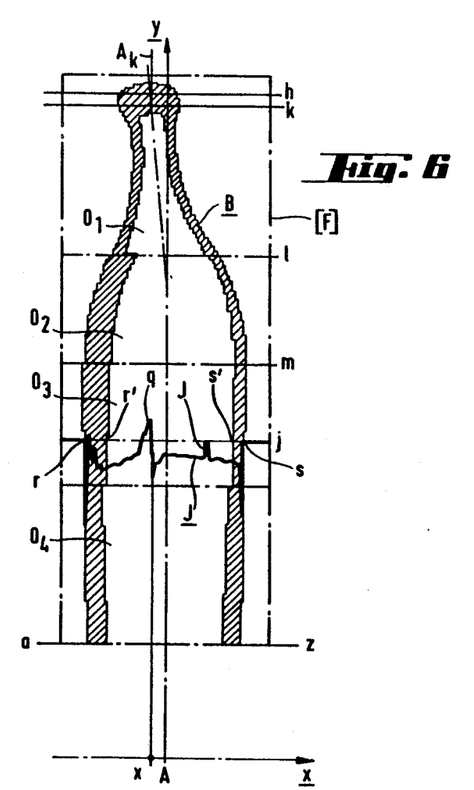
FIG. 6 is a depiction of the electronic image obtained with the apparatus of the present invention, and, FIG. 7 is a block diagram of the electronics of the machine.

Finally, as shown in FIG. 6 it is possible to reconstitute in the memory of the microcomputer an upright image B of each bottle and to display the characteristic anomalies opposite corrected coordinates. In particular, the image field specified by the movable window [C] can be plotted on a rectangular analysis grating [F] in which the effects of movement of the bottle are compensated for. In such a plot the vertical dimension y is deduced from the number of the scan line $v_j$ and the horizontal dimension X is calculated from $x=u_{ij}-wt_j$, in particular $A_j=a_j-wt_j$, referred to a reference instant 0..

To investigate defects, the test program examines the signals J (FIG. 6) that are received from the photodetector. The program ignores those signals that are produced during the initial rise of the mirror (slope $c_2$ of FIG. 5) and during dimensional measurements (plateau $c_5$ and $c_7$). It also ignores data generated near the edges of the object being inspected. The remaining data are then examined for anomalies by testing for anomalies of the direct type, the differential type, the integral type, etc., on the numerically converted values of the signal. The methods which can be used are conventional and they do not come within the scope of this invention. It is only necessary here to provide the general organization by indicating that the operation is carried out line by line, then from one line to another on successive elementary areas, starting from determined thresholds, themselves also obtained by learning but generally common to a whole series of successive lines. In this way, by recursion, the existence of the defects and their intensity are characterized and then, operating upon these elementary data, their shape, area and nature. Sensitivity of measurement as well as the calculation algorithm used in identifying the presence of an anomaly q and then the existence and nature of a defect Q can, of course, vary from one article to another and even from one area on an article to another according to need.

As will be apparent, the readings obtained from the photodetectors are only relative values which must be translated by reference to gauges and standards to determine if the bottles are good or, in contrast, carry a given defect. As a result, a learning stage, which may be manual or automatic, is needed to properly identify defects. These are conventional operations, which it is unnecessary to describe here.

It is clear also that every part of the wall of articles such as bottles is not viewed under the same conditions. The shadow at the edge of the image represents a progressive increase in obliquity and thickness of the glass through which the light passes. The thicker the wall, and the more opaque the glass is for the light used, the wider and darker this shadow is. In practice it allows defects to be detected only over 60 to 80% at most of the width of the image.

As a result, a single inspection is valid only for one-third or one-quarter approximately of the periphery at the rear and at the front of the bottle; and a complete inspection requires, in principle, two and more frequently three passages at complementary angles of presentation. For this reason, the present apparatus uses three successive stations, similar although not necessarily identical to each other, with appropriate rotation of the bottle between each station. These three stations may operate independently or in parallel and may have different lines of sight or different cycles. However, for each bottle the analysis is combined to determine if an instruction should be generated to eject the bottle from the conveyor.

Figure 7:
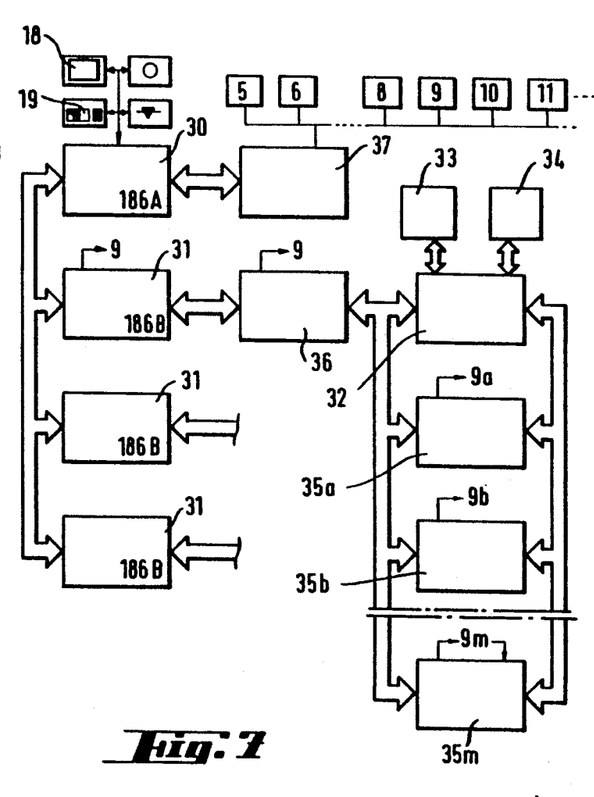

As shown in FIG. 7, the microcomputer comprises a central unit 30 equipped with suitable peripherals (keyboard 18, screen console 19, disc memory, printer, etc.). The microcomputer provides for the input and output both of the data for the program, the results of inspection, and also images of the articles. It controls the spacer, the ejector, alarms, etc., generates the CRT display, controls the velocities of the conveyor and the rotators, and, of course, controls the operating cycle of mirror 24 and photodetectors 23a. Central unit 30 which illustratively is an Intel 80186 microprocessor manages in parallel the three testing stations, the electronic circuits of which are identical. Accordingly, only one of these circuits is entirely shown in FIG. 7.

Each circuit is organized around a synthesis computer card 31 and further comprises an inspection card 32, in communication with control cards 33 for the camera and 34 for the mirror. The electric signals from the camera are stored by card 33. Line after line and in accordance with the instructions of the program, the card 31 creates and places the window [C$_j$] or, more exactly, resets the addresses i of the individual cells of this window so that the window is moved along with the image. Card 32 collects the luminous data J (FIG. 6) numerically stored by the card 33, picks up the extreme transitions and transmits the corresponding dimensional data. It thus generates the signal constituting the image of each object as shown in FIG. 6.

The processing of this image is carried out in the normal manner in the remainder of the circuit. The card 32 transmits the data to the parallel processing cards 35$a$ (amplitudes and differentiations), 35$b$ (envelopes and averages) ... 35$m$ (management of references data), for calculating differences q$a$, q$b$ ... inside each line and then those of the adjacent lines. An analysis card 36 manages these differences in the order of decreasing priorities a, b ..., enabling the information about dimensions and the information about anomalies q to be generated step by step as a function of the analysis program selected and then displayed as in FIG. 6 inside a grid supplying the true image B of the article.

The dimensional data and, where applicable, the type, amplitude and sign of the characteristic values q opposite their coordinates x, y are then picked up by the synthesis card 31 related to the station under consideration. This card regroups them on successive elementary areas of 4×4 mesh spacings, to generate the required information about defects Q: intensity, area, direction inside the inspection grating of the station, and therefore nature and seriousness.

The microprocessor 30 is then able to interpret the data collected, and, by means of a control card 37, to trigger the necessary actions at elements 5, 6 .... etc. of the apparatus shown in FIGS. 1–3.

Numerous variations may be employed in the practice of the invention. For example, a departure from symmetry caused by an oblique internal arrangement of certain of the members of a receiver could, in theory, compensate for example for the horizontal movement of the image during the course of the inspection. However, the disadvantages of this type of solution, especially its complication and lack of flexibility, appear to outweigh any advantages. Likewise, although it is conceivable to place the vertical planes of symmetry of two of the receivers obliquely to the line of the conveyor, this solution does not dispense with the need for some rotation of the article and possesses a whole series of serious disadvantages, especially in regard to the processing of the image.

On the other hand, the incorporation of auxiliary optical systems into the receiver can enable the field of vision of the receiver to be subdivided in order to observe the different zones of each article from independent angles, notably as a function of their level. In particular, sets of distribution mirrors parallel to the direction of the conveyor may be employed, similar to those which are mounted on the emitter in U.S. Pat. No. 4,620,090 in a different type of apparatus.

It would even be possible, in the limit, to make use of the vertical axis tracking mirror which the above patent describes, or again to rotate the articles continuously in front of the receivers. While three inspection stations would still be used, this would make the machine more compact by allowing the stations to be brought closer together. This, however, would be at the expense of accuracy.

At each station, it is possible to examine small articles in batches or, conversely, to carry out multiple inspections on the same article. For example, on thick or colored articles, it is possible to carry out two forward and return movements of mirror 24 in order to obtain, in each observation plane, two complementary angles of sight, offset by one-half of the field, in order to extend the effective area of investigation of defects.

While the invention has been described in terms of a linear camera having a longitudinal array of photodetectors that are physically parallel to the direction of movement of the conveyor, it will be appreciated that the invention may be practiced using other optical arrangements. In general, however, the optical arrangement should provide that the photodetector be scanned in substantially the same direction as any movement on the photodetector of the radiation that has passed through the object. Moreover, while a linear camera and scanning mirror are preferred for cost reasons as the means for providing a two-dimensional scan of the radiation from the object, the invention may also be practiced using a two-dimensional array of appropriate photodetectors such as a video camera.

Different techniques may be used to implement the windowing feature described in conjunction with FIG. 5. If the individual photodetectors of the camera are separately addressable, the window may be defined by specifying which photodetectors are to be addressed for each position of the image on the photodectors during the inspection cycle. Alternatively, signals from all the photodectors can be read out on a line-by-line basis and stored in memory and the window can be defined in terms of memory addresses which specify particular portions of the data from each scan line which are to be used in reconstructing the image. In either case the window can be moved electronically simply by incrementing address values and other techniques may be used if desired.

Numerous other variations in the practice of the invention will be apparent from the foregoing description to those skilled in the art.

What is claimed is:

1. A method of optically testing objects that are at least partially transparent comprising the steps of:

translating a line of the objects in a first direction through a first inspection station comprising a source of optical radiation on one side of the line of objects and an optical receiver on the other side of the line of objects, said source providing a substantially luminous intensity over an area greater than that of one of said objects;

directing onto a photosensitive means in said optical receiver radiation from said source that has passed through an object in said line, said photosensitive means extending in a second direction substantially parallel to said first direction;

generating from the radiation incident on said photosensitive means an electric signal representative of the radiation incident thereon by repetitively and rapidly scanning the photosensitive means electronically in said second direction and by more slowly sweeping the radiation that passed through the object across the photosensitive means in a third direction at an angle to the first direction.

2. The method of claim 1 wherein the photosensitive means is a linear network camera which is scanned to generate said electric signal.

3. The method of claim 2 wherein radiation is swept in said third direction by rotating a mirror that reflects radiation that passed through the object onto said camera.

4. The method of claim 3 further comprising the step of controlling the rotation of the mirror so as to vary the number of scans that are performed in the second direction per unit dimension of sweeping in the third direction.

5. The method of claim 1 wherein radiation is directed onto the photosensitive means by forming an image of the object on said photosensitive means.

6. The method of claim 1 wherein the radiation that passed through the object is swept in said third direction for a majority of the time the object is in the inspection station.

7. The method of claim 1 wherein the objects are inspected while moving in the first direction in the line.

8. The method of claim 1 wherein the radiation that passed through the object is swept in said third direction in accordance with a program specified by an operator.

9. The method of claim 1 further comprising the step of generating from the electric signal representative of the radiation incident on the photosensitive means a visual display of the object in the inspection station and any aberration in the radiation incident on said photosensitive means from said object.

10. The method of claim 9 wherein data originating at marginal zones of the objects are systematically erased.

11. The method of claim 1 wherein the third direction is perpendicular to the second direction.

12. A method of optically testing a plurality of at least partially transparent objects comprising the steps of:
   (a) translating the objects in a first direction in front of a source of optical radiation, said source providing a substantially luminous intensity over an area greater than that of one of said objects,
   (b) directing onto a photosensitive means radiation from said source that has passed through a first portion of at least one of said objects, said first portion extending in said first direction across the entire object and causing spatial variations in the radiation incident on the photosensitive means,
   (c) generating from the radiation incident on the photosensitive means from said first portion a time varying electric signal representative of the spatially varying radiation incident on the photosensitive means from said first portion by scanning said photosensitive means electronically, and
   (d) repeating steps (b) and (c) above for other portions of the same object, said portions being displaced from each other and from the first portion and extending in said first direction across the entire object.

13. The method of claim 12 wherein all of said portions are parallel to one another.

14. The method of claim 12 wherein the photosensitive means is raster-scanned.

15. The method of claim 12 wherein the photosensitive means is a linear network camera which is scanned to generate said time varying electric signal.

16. The method of claim 12 wherein steps (b) and (c) are repeated for other portions of the same object by rotating a mirror that reflects onto the camera radiation that passed through different portions of the object.

17. The method of claim 12 further comprising the step of varying the rate of the rotation of the mirror.

18. The method of claim 12 wherein radiation is directed onto the photosensitive means by forming an image of the object on said photosensitive means.

19. The method of claim 12 further comprising the step of generating from the electric signal representative of the radiation incident on the photosensitive means a visual display of the object and any aberration in the radiation incident on said photosensitive means from said object.

20. A method of optically testing a plurality of at least partially transparent objects comprising the steps of:
   translating the objects past a source of optical radiation, said source, providing a substantially luminous intensity over an area greater than that of one of said objects,
   forming an image on a first part of a linear photosensitive means with radiation from said source that has passed through at least one of said objects, said object causing spatial variations in the image on the photosensitive means, said photosensitive means extending in a first direction and said image moving in said first direction on the photosensitive means because of movement of the object past the source of radiation, and
   generating from the moving image on the photosensitive means a time varying electric signal representative of the spatial variations in the image by sweeping an image of the object in a second direction across the photosensitive means and by using the electric signal from only the first part of the photosensitive means on which the moving image is incident.

21. The method of claim 20 wherein the photosensitive means is a linear network camera comprising a plurality of photodectors which extend in said first direction and are scanned to generate said time varying electric signal.

22. The method of claim 21 wherein a window is defined on the photodetectors so that only some of them are used to produce said electric signal at any time and the window is moved electronically in step with the image as the image moves across the photodetectors.

23. The method of claim 21 wherein the image is swept in a second direction at an angle to the first direction by rotating a mirror that reflects onto the camera radiation that passed through the object.

24. The method of claim 23 further comprising the step of controlling the rotation of the mirror so as to vary the number of scans that are performed in the first direction per unit dimension of sweeping in the second direction.

25. The method of claim 20 further comprising the step of generating from the electric signal representative of the radiation incident on the photosensitive means a visual display of the object and any aberration in the radiation incident on said photosensitive means from said object.

26. The method of claim 20 wherein an object moves a distance greater than its diameter between commencement and termination of scanning of its image.

27. A device for optical testing of objects moving in a first direction in a line on a conveyor comprising:
   a source of optical radiation on one side of the conveyor, said source providing a substantially luminous intensity over an area greater than that of one of said objects, a receiver on an opposite side of the conveyor and aligned with the source so that radiation from said source that passes through an object on the conveyor is incident on said receiver, said receiver extending in a second direction substantially parallel to said first direction, means for electronically scanning the radiation incident on said receiver in said second direction, and means for mechanically sweeping the radiation incident on said receiver in a third direction at an angle to said first direction.

28. The device of claim 27 further comprising auxiliary optical systems in the receiver that subdivides its field of view for observing various zones of each object from independent angles.

29. The device of claim 27 wherein the receiver is a linear network camera having a row of photosensitive cells oriented in said second direction.

30. The device of claim 27 wherein the means for sweeping the radiation in the third direction comprises a pivoting member mounted on a shaft that is moved by a programmable mechanism.

31. The device of claim 30 wherein the programmable mechanism comprises a moving coil galvanometer supplied with an adjustable voltage from a numerically controlled voltage divider.

32. The device of claim 30 wherein the pivoting member is a plane mirror which reflects radiation that has passed through different parts of the objects on the conveyor to a photosensitive means in the receiver.

33. The device of claim 30 wherein the conveyor is a horizontal table conveyor and a horizontal field of the receiver covers a width at least approximately 2.5 times the apparent width of individual objects on the conveyor.

34. The device of claim 30 wherein the receiver comprises a linear camera and the means for scanning radiation in a second direction comprises means for successively reading individual photosensitive cells in said camera on which is incident radiation that has passed through an object on said conveyor.

35. The device of claim 34 wherein the object is moving as it is being scanned, thereby causing the radiation from the object to move across the individual photosensitive cells of the linear camera, further comprising means for changing the individual cells that are read as the radiation from the object moves across the cells.

36. The device of claim 34 further comprising means for forming on the receiver an image of the object which moves in said second direction as the object moves on the conveyor.

37. The device of claim 27 further comprising means for generating an electrical signal representative of the radiation incident on the receiver.

38. The device of claim 37 further comprising means for generating from said electrical signal a visual display of the object on the conveyor and any aberration in the radiation incident on said receiver from said object.

39. Apparatus for optically testing objects that are at least partially transparent comprising:

means for translating a line of the objects in a first direction through a first inspection station comprising a source of optical radiation on one side of the line of objects and an optical receiver on the other side of the line of objects, said source providing a substantially luminous intensity over an area greater than that of one of said objects;

means for directing onto a photosensitive means in said optical receiver radiation from said source that has passed through an object in said line, said photosensitive means extending in a second direction substantially parallel to said first direction; and means for generating from the radiation incident on said photosensitive means an electric signal representative of the radiation incident thereon by repetitively and rapidly scanning the photosensitive means electronically in said second direction and by more slowly seeping the radiation that passed through the object across the photosensitive mean sin a third direction at an angle to the first direction.

40. Apparatus for optically testing a plurality of at least partially transparent objects comprising:

means for translating the objects in a first direction in front of a source of optical radiation, said source providing a substantially luminous intensity over an area greater than that of one of said objects, means for directing onto a photosensitive means radiation from said source that has passed through a first portion of at least one of said objects, said first portion extending in said first direction across the entire object and causing spatial variations in the radiation incident on the photosensitive means, means for generating from the radiation incident on the photosensitive means that has passed through said first portion a time varying electric signal representative of the spatially varying radiation incident on the photosensitive means from said first portion by scanning said photosensitive means electronically, and means for directing onto the photosensitive means radiation that has passed through other portions of the same object, said portions being displaced from each other and from the first portion and extending in said first direction across the entire object.

41. Apparatus for optically testing a plurality of at least partially transparent objects comprising:

a source of optical radiation, means for translating the objects past the source of optical radiation, said source providing a substantially luminous intensity over an area greater than that of one of said objects, means for forming an image on a first part of a linear photosensitive means with radiation from said source that has passed through at least one of said objects, said object causing spatial variations in the image on the photosensitive means, said photosensitive menas extending in a first direction and said image moving in said first direction on the photosensitive means because of movement of the object past the source of radiation, and means for generating from the moving image on the photosensitive means a time varying electric signal representative of the spatial variations in the image by sweeping an image of the object in a second direction across the photosensitive means and by using the electric signal from only the first part of the photosensitive means on which the moving image is incident.

42. The apparatus of claim 41 wherein the photosensitive means is a linear network camera comprising a plurality of photodectors which extend in said first direction and are scanned to generate said time varying electric signal.

43. The apparatus of claim 42 wherein the generating means comprises means for defining a window on the photodetectors so that only some of them are used to produce said electric signal at any time and the window is moved electronically as the image moves across the photodetectors.

* * * * *